(12) United States Patent
Gerdes et al.

(10) Patent No.: US 9,591,818 B2
(45) Date of Patent: *Mar. 14, 2017

(54) LOW SATURATED-FAT SUNFLOWER AND ASSOCIATED METHODS

(75) Inventors: James T. Gerdes, Breckenridge, MN (US); Charles J. Kahl, Westfield, IN (US); Angela L. Erickson, Fergus Falls, MN (US); Robert M. Benson, Ellsworth, WI (US)

(73) Assignee: Dow AgroSciences LLC, Indianapolis, IN (US)

( * ) Notice: Subject to any disclaimer, the term of this patent is extended or adjusted under 35 U.S.C. 154(b) by 909 days.

This patent is subject to a terminal disclaimer.

(21) Appl. No.: 12/340,525

(22) Filed: Dec. 19, 2008

(65) Prior Publication Data

US 2009/0181149 A1    Jul. 16, 2009

Related U.S. Application Data

(60) Provisional application No. 61/015,591, filed on Dec. 20, 2007.

(51) Int. Cl.
*A01H 5/10* (2006.01)
*C12N 15/82* (2006.01)
*A01H 5/00* (2006.01)

(52) U.S. Cl.
CPC ............... *A01H 5/10* (2013.01); *A01H 5/00* (2013.01); *C12N 15/82* (2013.01)

(58) Field of Classification Search
None
See application file for complete search history.

(56) References Cited

U.S. PATENT DOCUMENTS

| | | | |
|---|---|---|---|
| 5,276,264 A | 1/1994 | Heaton et al. | |
| 5,387,758 A | 2/1995 | Wong et al. | |
| 5,912,416 A | 6/1999 | Weisker | |
| 6,162,965 A | 12/2000 | Hansen | |
| 6,175,065 B1 | 1/2001 | Schmidt et al. | |
| 6,229,056 B1 | 5/2001 | Ansmann et al. | |
| 6,956,156 B2 | 10/2005 | Gerdes et al. | |
| 6,977,328 B2 | 12/2005 | Gerdes et al. | |

FOREIGN PATENT DOCUMENTS

| | | |
|---|---|---|
| CA | 2058849 A1 | 7/1992 |
| CN | 1636440 | 7/2005 |
| EP | 0496504 A1 * | 7/1992 |
| EP | 1598422 | 12/2005 |
| RU | 2147407 | 4/2000 |
| WO | 2007/107807 A1 | 9/2007 |

OTHER PUBLICATIONS

Glenn et al. (FETT, 10(4-5):177-181).*
PCT Search Report and Written Opinion for PCT/US2008/087827, mailed May 12, 2009, 21 pages.
Cole Glenn et al., "New Sunflower and Soybean Cultivars for Novel Vegetable Oil Types", FETT, vol. 100, No. 4-5, May 1998, pp. 177-181, XP009115773, ISSN: 0931-5985.
Seiler G., "Wild Perennial Sunflower as a Potential Source of Reduced Palmitic and Stearic Fatty Acids in Sunflower Oil", Helia, vol. 25, No. 36, 2002, pp. 79-84, XP009115736.
Vick B. et al., "Inheritance of Reduced Saturated Fatty Acid Content in Sunflower Oil", Helia, vol. 25, No. 36, 2002, pp. 113-122, XP009115735.
Simpson B.W. et al., "Selection for High Linoleic Acid Content in Sunflower Helianthus-Annuus L", Australian Journal of Experimental Agriculture, vol. 29, No. 2, 1989, pp. 233-240, XP009115729.
Collard et al.; Marker-assisted selection: an approach for precision plant breeding in the twenty-first century; Philosophical Transactions of the Royal Society B (2008) 363, 557-572.
Rosyara, U.R.; Requirement of Robust Molecular Marker Technology for Plant Breeding Applications; Journal of Plant Breeding Gourp 1: 67-72, 2006.
Ramos-Gomez et al.; Development of a method to recovery and amplification DNA by real-time PCR from commercial vegetable oils; Food Chemistry 158 (2014) 374-383.

* cited by examiner

*Primary Examiner* — Vinod Kumar
(74) *Attorney, Agent, or Firm* — Carl D. Corvin; Magleby Cataxinos & Greenwood

(57) ABSTRACT

Provided are sunflowers, parts thereof, cultures of, and seeds that are capable of producing sunflower oil that is low in saturated fat and, optionally, high in linoleic acid as well as associated methods.

1 Claim, 3 Drawing Sheets

```
332.
332.5   (1)   ----------------------------------------------------------------------AGCTCAC
333.1   (1)   ----------------------------------------------------------------------AGCTCAC
333.2   (1)   ----------------------------------------------------------------------AGCTCAC 332.4   (8)   AAAGCACTTGAGATGGCAGAGGTTGATGCTGATGATGTGGATCTACTTCTTTTATGCACATCGACCCCGGATGAT
332.5   (8)   AAAGCACTTGAGATGGCAGAGGTTGATGCTGATGATGTGGATCTACTTCTTTTATGCACATCGACCCCGGATGAT
333.1   (8)   AAAGCACTTGAGATGGCAGAGGTTGATGCTGATGATGTGGATCTACTTCTTTTATGCACATCGACCCCGGATGAT
333.2   (8)   AAAGCACTTGAGATGGCAGAGGTTGATGCTGATGATGTGGATCTACTTCTTTTATGCACATCGACCCCGGATGAT 332.4   (83)  CTATTTGGTAGTGCTCCACAGGTATTGCTTCAAATTCTTGCAGAAGATAGATGTTTTCAAATGTGCCTAAAAAGG
332.5   (83)  CTATTTGGTAGTGCTCCACAGGTATTGCTTCAAATTCTTGCAGAAGATAGATGTTTTCAAATGTGCCTAAAAAGG
333.1   (83)  CTATTTGGTAGTGCTCCACAGGTATTGCTTCAAATTCTTGCACAAGATAGATGTTT------------------
333.2   (83)  CTATTTGGTAGTGCTCCACAGGTATTGCTTCAAATTCTCGCACAAGATAGATGTTT------------------

332.4   (158) TTTCATTTTTT-AATTTTAGTGGGATGTCCTGAGAAAAAAATTGTTGCAGTATTTATGGAATTAAAAAAGTATTT
332.5   (158) TTTCATTTTTTTAATTTTAGTGGGATGTCCTGAGAAAAAAATTGTTGCAGTATTTATGGAATTAAAAAAGTATTT
333.1   (139) -------------------------GTCCTGAGAAAAAAACTGTTGCAGTATTTATGGAATTAAAAAAGTATTT
333.2   (139) -------------------------GTCCTGAGAAAAAAACTGTTGCAGTATTTATGGAATTAAAAAAGTATTT 332.4   (232) GTGTTGTATATAGAAATATTTGACTGCATATAATTTTCTTGTTGAATAATTGGCAATGATTTTAACATTTTTTTT
332.5   (233) GTGTTGTATATAGAAATATTTGACTGCATATAATTTTCTTGTTGAATAATTGGCAATGATTTTAACATTTTTTTT
333.1   (188) GTGTTGTATATAGAAATATTTGACTGCATATAATTTTCTTGTTGAATAATTGGCAATGATTTTAACATTTTTTTT
333.2   (188) GTGTTGTATATAGAAATATTTGACTGCATATAATTTTCTTGTTGAATAATTGGCAATGATTTTAACATTTTTTTT 332.4   (307) CTTATATGGTAATCTCAACGCGTTCCTGAATTTTTGTATGTTTCTACCGGCTGTAGACTTTAGATTTCTACAGTT
332.5   (308) CTTATATGGTAATCTCAACGCGTTCCTGAATTTTTGTATGTTTCTACCGGCTGTAGACTTTAGATTTCTACAGTT
333.1   (263) CTTATATGGTAATCTCAACGCGTTCCTGAATTTTTGTATGTTTCTACTGGCTGTAGACTTTAGATTTCTACAGTT
333.2   (263) CTTATATGGTAATCTCAACGCGTTCCTGAATTTTTGTAAGTTTCTACTGGCTGTAGACTTTAGATTTCTACAGTT 332.4   (382) --------TGATCATGATCCAATTTTCAAAAGTTTTTTTTTAA-AAAGATTAATCTGTGTACATTATAGGTGAA
332.5   (383) --------TGATCATGATCCAATTTTCAAAAGTTTTTTTTTAA-AAAGATTAATCTGTGTACATTATAGGTGAA
333.1   (338) CTACAGTTTGATCATGATCCAATTTTCAATTTTTTTTTTTTTTAAAGATTAATCTGTGTACATTATAGGTGAA
333.2   (338) CTACAGTTTGATCATGATCCAATTTTCAATTTTTTTTTTTTTTAAAGATTAATCTGTGTACATTATAGGTGAA 332.4   (448) AAAATGGGCCGGAGGGGTGGATTCTTTTAAGTTTTAACATGTTAAATATGGGTAACTTTTTATACGGATCGAAAC
332.5   (449) AAAATGGGCCGGAGGGGTGGATTCTTTTAAGTTTTAACATGTTAAATATGGGTAACTTTTTATACGGATCGAAAC
333.1   (413) AAAATGGGCCAGAGGGGTGGATTTTTTT-------AACATGTTAAAAATGGGGAACTTTTTATACGGATCGAATC
333.2   (413) AAAATGGGCCAGAGGGGTGGATTTTTTT-------AACATGTTAAAAATGGGGAACTTTTTATACGGATCGAATC 332.4   (523) ATCAAAATGGGTTGGGTTCACCTGAAACACTTCCTCTCGAAATATTCTATTAATAAATAGTTGTATGATTACAAA
332.5   (524) ATCAAAATGGGTTGGGTTCACCCGAAACACTTCCTCTCGAAATATTCTATTAATAAATAGTTGTATGATTACAAA
333.1   (481) ATCAAAATGGGTTGGGTTCACCCGAAACACTTCCTCTCCAAATATTGTATTAATAAATAGTTGTATGATTACAAA
333.2   (481) ATCAAAATGGGTTGGGTTCACCCGAAACACTTCCTCTCCAAATATTGTATTAATAAATAGTTGTATGATTACAAA 332.4   (598) CATTAAATATTTTCAACAATATTTTTTTAATAAATTGGCTTATGAGGTTTATTGCTTAAAGTTTCACTTTGGGTA
332.5   (599) CATTAAATATTTTCAACAATATTTTTTTAATAAATTGGCTTATGAGGTTTATTGCTTAAAGTTTCACTTTGGGTA
333.1   (556) CATTAAATATTTTCAACAATATTTTTT-AACAAATTGGCTTATGAGGTTTATTGCTTAACGTTTTACTTTGGGTA
333.2   (556) CATTAAATATTTTCAACAATATTTTTT-AACAAATTGGCTTATGAGGTTTATTGCTTAACGTTTTACTTTGGGCA 332.4   (673) TTTTTTTCCGGTTGACCCGTTTGACTCATTTTTTCTTTAACTGCTTTTTAACCCACCCATTTGACCTTTTAGAAA
332.5   (674) TTTTTTTCCGGTTGACCCGTTTGACTCATTTTTTCTTTAACTGCTTTTTAACCCACCCATTTGACCTTTTAGAAA
333.1   (630) ATTTTTTCCGGTTGACCCGTTTGACTCATTTTCTCTTTAACTGCTTTTTAACCCACCCATTTGACCTTTTAGAAA
333.2   (630) ATTTTTTCCGGTTGACCCGTTTGACTCATTTTCTCTTTAACTGCTTTTTAACCCACCCATTTGACCTTTTAGAAA 332.4   (748) AAAAACACATAACCCGAATAGATCTTTTCATAAGTAAATTGGTGTATGTAAACCGCCACCTCTAGTATTTTAAGA
332.5   (749) AAAAACACATAACCCGAATAGATCTTTTCATAAGTAAATTGGTGTATGTAAACCGCCACCTCTAGTATTTTAAGA
333.1   (705) AAAAAAAAAAAAA-----AAACATA-----ACCCGAATATTGGTGTATGTTAACTGCCACCTCTAGTATTTTAAGA
333.2   (705) AAAAAAAAAAAAA-----AAACATA-----ACCCGAATATTGGTGTATGTTAACTGCCACCTCTAGTATTTTAAGA 332.4   (823) AAATCTACATTAATTTTGAAAATGAAACGAGTTACTTAATTTGAACTTGTAATCAGATACAAGCCGCACTCGGGT
332.5   (824) AAATCTACATTAATTTTGAAAATGAAACAAGTTACTTAATTTGAACTTGTAATCAGATACAAGCCGCACTCGGGT
333.1   (770) AAATCTACATTAATTTTGAAAATGAAACAAGTTACTTAATTTGAACTTGTAATCAGATACAAGCCGCACTCGGGT
333.2   (770) AAATCTACATTAATTTTGAAAATGAAACAAGTTACTTAATTTGAACTTGTAATCAGATACAAGCCGCACTCGGGT 332.4   (898) GCAAGGGAAATCCATTGC[CA]TTGATATTACAGCTGCTTGTAGTGGATTTGTTTGGGTCTAGTCTCAGCTTCGT
332.5   (899) GCAAGGGAAATCCATTGC[CA]TTGATATTACAGCTGCTTGTAGTGGATTTGTTTGGGTCTAGTCTCAGCTTCGT
333.1   (845) GCAAGGGAAATCCATTGC[CG]TTGATATTACAGCTGCTTGTAGTGGATTTGTTTGGGTCTAGTCTCAGCTTCGT
333.2   (845) GCAAGGGAAATCCATTGC[CG]TTGATATTACAGCTGCTTGTAGTGGATTTGTTTGGGTCTAGTCTCAGCTTCGT 332.4   (973) GTTATATCCG
332.5   (974) GTTATATCCG
333.1   (920) GTTATATCCG
333.2   (920) GTTATATCCG
```

FIG 2

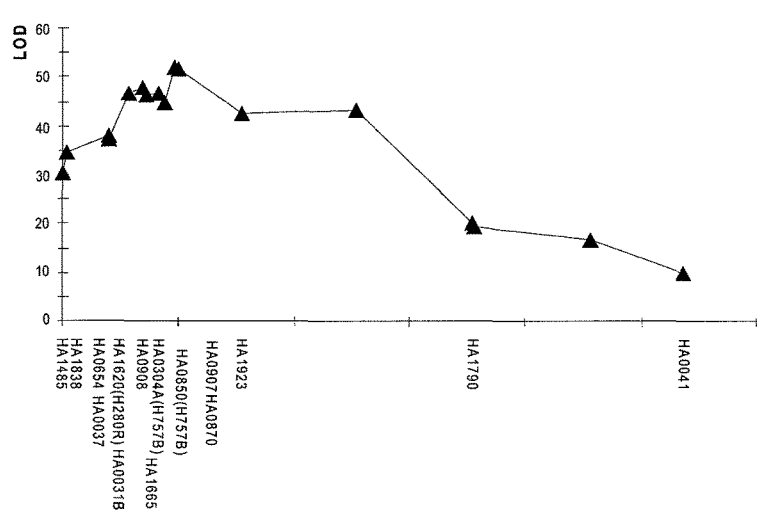
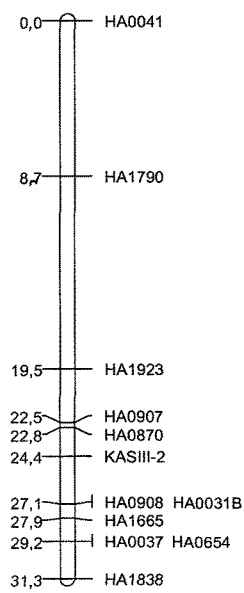
FIG 3

```
                    SEQUENCE LISTING

<160> NUMBER OF SEQ ID NOS: 41

<210> SEQ ID NO 1
<211> LENGTH: 22
<212> TYPE: DNA
<213> ORGANISM: Artificial Sequence
<220> FEATURE:
<223> OTHER INFORMATION: Chemically Synthesized - HA0442 Forward Primer

<400> SEQUENCE: 1
tggaactgta aatggaccca ag                                              22

<210> SEQ ID NO 2
<211> LENGTH: 22
<212> TYPE: DNA
<213> ORGANISM: Artificial Sequence
<220> FEATURE:
<223> OTHER INFORMATION: Chemically Synthesized - HA0442 Reverse Primer

<400> SEQUENCE: 2
gcactgcacc atttatgaga ag                                              22

<210> SEQ ID NO 3
<211> LENGTH: 24
<212> TYPE: DNA
<213> ORGANISM: Artificial Sequence
```

```
<220> FEATURE:
<223> OTHER INFORMATION: Chemically Synthesized - CRT22 Forward Primer

<400> SEQUENCE: 3
tcgagatgaa accgaatgaa gaaa                                              24

<210> SEQ ID NO 4
<211> LENGTH: 29
<212> TYPE: DNA
<213> ORGANISM: Artificial Sequence
<220> FEATURE:
<223> OTHER INFORMATION: Chemically Synthesized - CRT22 Reverse Primer

<400> SEQUENCE: 4
gtttcttggg actgatattg ccaagtggg                                         29

<210> SEQ ID NO 5
<211> LENGTH: 22
<212> TYPE: DNA
<213> ORGANISM: Artificial Sequence
<220> FEATURE:
<223> OTHER INFORMATION: Chemically Synthesized - ORS565 Forward Primer

<400> SEQUENCE: 5
tggtcaacgg atttagagtc aa                                                22

<210> SEQ ID NO 6
<211> LENGTH: 21
<212> TYPE: DNA
<213> ORGANISM: Artificial Sequence
<220> FEATURE:
<223> OTHER INFORMATION: Chemically Synthesized - ORS565 Reverse Primer

<400> SEQUENCE: 6
tccagtttgg tcttgatttg g                                                 21

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized - ORS732 Forward Primer

<400> SEQUENCE: 7
gcacggaact cctcaaatgt                                                   20

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized - ORS732 Reverse Primer

<400> SEQUENCE: 8
gcacgggaaa caaagagtca                                                   20

<210> SEQ ID NO 9
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 9
ccggctgctt ctagacctta taag                                              24
```

```
<210> SEQ ID NO 10
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 10
tcgtcggtgg gacacaca                                                   18

<210> SEQ ID NO 11
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 11
actgttggat cggttc                                                     16

<210> SEQ ID NO 12
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 12
cactgttgga tcgatt                                                     16

<210> SEQ ID NO 13
<211> LENGTH: 355
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (60)..(60)
<223> OTHER INFORMATION: n can be either T or C
<220> FEATURE:
<221> NAME/KEY: misc_feature
<222> LOCATION: (181)..(181)
<223> OTHER INFORMATION: n can be either A or G
<220> FEATURE:
<221> NAME/KEY: misc_feature
<222> LOCATION: (258)..(260)
<223> OTHER INFORMATION: n can be either T or C
<220> FEATURE:
<221> NAME/KEY: misc_feature
<222> LOCATION: (261)..(261)
<223> OTHER INFORMATION: n can be either T or C

<400> SEQUENCE: 13
ttattctcgg cttccggtgt gattttactc tcatggttaa gttttcaaga gattgtcgcn     60
gctgaaaact ttttatattg tttcggtatg atcttggagt ttatagcctt tgtaaggtta    120
agaatgaaac acccggctgc ttctagacct tataagatac ccgtgggcac tgttggatcg    180
nttcttctgt gtgtcccacc gacgattttg atctgtgtcg tgttggctct tcttcactc    240 aaggtcatga tcgttagngt nattgccata tttttcgggt tcgcattgca accgttttta    300
aagtttgccg agaagaaaag atggcttaaa ttttcaacta aagccgatct tcccg         355

<210> SEQ ID NO 14
<211> LENGTH: 23
<212> TYPE: DNA
<213> ORGANISM: Artificial Sequence
```

<220> FEATURE:
<223> OTHER INFORMATION: Chemically Synthesized

<400> SEQUENCE: 14
gtccatcttt cctcaacgac ttg                                              23

<210> SEQ ID NO 15
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 15
cctaaacgcc tcgaaaaagc t                                                21

<210> SEQ ID NO 16
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 16
ttaccatgtc tataatgc                                                    18

<210> SEQ ID NO 17
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 17
attaccatgt ctgtaatgc                                                   19

<210> SEQ ID NO 18
<211> LENGTH: 539
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (299)..(299)
<223> OTHER INFORMATION: n can be G or A
<220> FEATURE:
<221> NAME/KEY: misc_feature
<222> LOCATION: (364)..(364)
<223> OTHER INFORMATION: n can be T or C
<220> FEATURE:
<221> NAME/KEY: misc_feature
<222> LOCATION: (439)..(439)
<223> OTHER INFORMATION: n can be T or C
<220> FEATURE:
<221> NAME/KEY: misc_feature
<222> LOCATION: (457)..(457)
<223> OTHER INFORMATION: n can be G or A

<400> SEQUENCE: 18
aactgagttc tgtacgccag agatttgccc gaccatgacc gcaggtccaa agtaagtctt      60
gctattgcac atttgcacga ttaacggttt cttatataga agatacatga ttcttgaatt     120
tatgtaaata aaacttgaca gatatgaata ccgatgggct gatggtgtgc aaatcaagaa     180
gcctattgaa gtttcggctc caaagtacgt agagttcttg atggattgga ttgagtcaca     240
attggatgac gagtccatct ttcctcaacg acttggtaat tagttaatta ccatgtctnt     300

```
aatgcatcat ttaataaagc tttttcgagg cgtttaggaa actgaaatag taattttcga    360
ttgncgtgca ggagcgccat ttcccgccaa ttttagggac gttgtgaaaa cgatatttaa    420
acgcttgttt cgtgtatang cgcatatcta ccacacncat tttcagaaga ttgtgagtct    480
taaagaagaa gcccatctaa acacttgttt caagcatttc atattgttta catgtgtaa     539
```

```
<210> SEQ ID NO 19
<211> LENGTH: 20
<212> TYPE: DNA
<213> ORGANISM: Artificial Sequence
<220> FEATURE:
<223> OTHER INFORMATION: Chemically Synthesized - HT57F

<400> SEQUENCE: 19
gcgattattg ttatggacgc                                                 20

<210> SEQ ID NO 20
<211> LENGTH: 20
<212> TYPE: DNA
<213> ORGANISM: Artificial Sequence
<220> FEATURE:
<223> OTHER INFORMATION: Chemically Synthesized - HT57R

<400> SEQUENCE: 20
agcggaaact gttcttgttg                                                 20

<210> SEQ ID NO 21
<211> LENGTH: 18
<212> TYPE: DNA
<213> ORGANISM: Artificial Sequence
<220> FEATURE:
<223> OTHER INFORMATION: Chemically Synthesized - HT64F

<400> SEQUENCE: 21
ttattctcgg cttccggt                                                   18

<210> SEQ ID NO 22
<211> LENGTH: 18
<212> TYPE: DNA
<213> ORGANISM: Artificial Sequence
<220> FEATURE:
<223> OTHER INFORMATION: Chemically Synthesized - HT64R

<400> SEQUENCE: 22
cgggaagatc ggctttag                                                   18

<210> SEQ ID NO 23
<211> LENGTH: 20
<212> TYPE: DNA
<213> ORGANISM: Artificial Sequence
<220> FEATURE:
<223> OTHER INFORMATION: Chemically Synthesized - HT131F

<400> SEQUENCE: 23
cgtaacatgc aagttgtgga                                                 20

<210> SEQ ID NO 24
<211> LENGTH: 20
<212> TYPE: DNA
<213> ORGANISM: Artificial Sequence
<220> FEATURE:
<223> OTHER INFORMATION: Chemically Synthesized - HT131R

<400> SEQUENCE: 24
tgtactctaa acgggcaacc                                                 20
```

<210> SEQ ID NO 25
<211> LENGTH: 20
<212> TYPE: DNA
<213> ORGANISM: Artificial Sequence
<220> FEATURE:
<223> OTHER INFORMATION: Chemically Synthesized - HT134F

<400> SEQUENCE: 25
agtcatgctt gaaggagctg                                        20

<210> SEQ ID NO 26
<211> LENGTH: 20
<212> TYPE: DNA
<213> ORGANISM: Artificial Sequence
<220> FEATURE:
<223> OTHER INFORMATION: Chemically Synthesized - HT134R

<400> SEQUENCE: 26
ctctgtcagc ttgcaatgaa                                        20

<210> SEQ ID NO 27
<211> LENGTH: 20
<212> TYPE: DNA
<213> ORGANISM: Artificial Sequence
<220> FEATURE:
<223> OTHER INFORMATION: Chemically Synthesized - HT210F

<400> SEQUENCE: 27
ctaaaactgt cgcaagggaa                                        20

<210> SEQ ID NO 28
<211> LENGTH: 20
<212> TYPE: DNA
<213> ORGANISM: Artificial Sequence
<220> FEATURE:
<223> OTHER INFORMATION: Chemically Synthesized - HT210R

<400> SEQUENCE: 28
cctccatcaa tggtaagcac                                        20

<210> SEQ ID NO 29
<211> LENGTH: 21
<212> TYPE: DNA
<213> ORGANISM: Artificial Sequence
<220> FEATURE:
<223> OTHER INFORMATION: Chemically Synthesized - ZVG76snpF

<400> SEQUENCE: 29
tccaactcat gaacggactc t                                      21

<210> SEQ ID NO 30
<211> LENGTH: 20
<212> TYPE: DNA
<213> ORGANISM: Artificial Sequence
<220> FEATURE:
<223> OTHER INFORMATION: Chemically Synthesized - ZVG77snpF

<400> SEQUENCE: 30
ttggtgactc ttgcagcatc                                        20

<210> SEQ ID NO 31
<211> LENGTH: 20
<212> TYPE: DNA
<213> ORGANISM: Artificial Sequence
<220> FEATURE:

<223> OTHER INFORMATION: Chemically Synthesized - ZVG77snpR

<400> SEQUENCE: 31
aagtttaaaa ccgcgtcgtg                                              20

<210> SEQ ID NO 32
<211> LENGTH: 20
<212> TYPE: DNA
<213> ORGANISM: Artificial Sequence
<220> FEATURE:
<223> OTHER INFORMATION: Chemically Synthesized - ZVG78snpF

<400> SEQUENCE: 32
tatgagcctc ttcggtctcg                                              20

<210> SEQ ID NO 33
<211> LENGTH: 20
<212> TYPE: DNA
<213> ORGANISM: Artificial Sequence
<220> FEATURE:
<223> OTHER INFORMATION: Chemically Synthesized - ZVG78snpR

<400> SEQUENCE: 33
caccttattc agccccgata                                              20

<210> SEQ ID NO 34
<211> LENGTH: 20
<212> TYPE: DNA
<213> ORGANISM: Artificial Sequence
<220> FEATURE:
<223> OTHER INFORMATION: Chemically Synthesized - HA0953F-HEX

<400> SEQUENCE: 34
caaaccaaca accaccatca                                              20

<210> SEQ ID NO 35
<211> LENGTH: 20
<212> TYPE: DNA
<213> ORGANISM: Artificial Sequence
<220> FEATURE:
<223> OTHER INFORMATION: Chemically Synthesized - HA0953R

<400> SEQUENCE: 35
aaacgacacc gatgagaacc                                              20

<210> SEQ ID NO 36
<211> LENGTH: 26
<212> TYPE: DNA
<213> ORGANISM: Artificial Sequence
<220> FEATURE:
<223> OTHER INFORMATION: Chemically Synthesized - HA1909F-FAM

<400> SEQUENCE: 36
ctgagtttcg tgtaccattt ctattg                                       26

<210> SEQ ID NO 37
<211> LENGTH: 22
<212> TYPE: DNA
<213> ORGANISM: Artificial Sequence
<220> FEATURE:
<223> OTHER INFORMATION: Chemically Synthesized - HA1909R

<400> SEQUENCE: 37
acaccaatca gtgggtttca tc                                           22

<210> SEQ ID NO 38
<211> LENGTH: 929
<212> TYPE: DNA
<213> ORGANISM: Artificial Sequence
<220> FEATURE:
<223> OTHER INFORMATION: Chemically Synthesized -

<400> SEQUENCE: 38

```
agctcacaaa gcacttgaga tggcagaggt tgatgctgat gatgtggatc tacttctttt      60
atgcacatcg accccggatg atctatttgg tagtgctcca caggtattgc ttcaaattct     120
tgcacaagat agatgtttgt cctgagaaaa aaactgttgc agtatttatg gaattaaaaa     180
agtatttgtg ttgtatatag aaatatttga ctgcatataa ttttcttgtt gaataattgg     240
caatgatttt aacatttttt ttcttatatg gtaatctcaa cgcgttcctg aattttttgta     300
agtttctact ggctgtagac tttagatttc tacagttcta cagtttgatc atgatccaat     360
tttcaatttt ttttttttt ttaaagatta atctgtgtac attataggtg aaaaaatggg      420
ccagaggggt ggattttttt aacatgttaa aaatggggaa cttttttatac ggatcgaatc     480
atcaaaatgg gttgggttca cccgaaacac ttcctctcca atattgtat taataaatag      540
ttgtatgatt acaaacatta aatattttca acaatatttt ttaacaaatt ggcttatgag     600
gtttattgct taacgtttta ctttgggtaa ttttttccgg ttgacccgtt tgactcattt     660
tctctttaac tgcttttaa cccacccatt tgacctttta gaaaaaaaa aaaaaaaaac       720
ataacccgaa tattggtgta tgttaactgc cacctctagt attttaagaa aatctacatt     780
aattttgaaa atgaaacaag ttacttaatt tgaacttgta atcagataca agccgcactc     840
gggtgcaagg gaaatccatt ggcgtttgat attacagctg cttgtagtgg atttgttttg     900
ggtctagtct cagcttcgtg ttatatccg                                         929
```

<210> SEQ ID NO 39
<211> LENGTH: 929
<212> TYPE: DNA
<213> ORGANISM: Artificial Sequence
<220> FEATURE:
<223> OTHER INFORMATION: Chemically Synthesized -

<400> SEQUENCE: 39

```
agctcacaaa gcacttgaga tggcagaggt tgatgctgat gatgtggatc tacttctttt      60
atgcacatcg accccggatg atctatttgg tagtgctcca caggtattgc ttcaaattct     120
cgcacaagat agatgtttgt cctgagaaaa aaactgttgc agtatttatg gaattaaaaa     180
agtatttgtg ttgtatatag aaatatttga ctgcatataa ttttcttgtt gaataattgg     240
caatgatttt aacatttttt ttcttatatg gtaatctcaa cgcgttcctg aattttttgta     300
agtttctact ggctgtagac tttagatttc tacagttcta cagtttgatc atgatccaat     360
tttcaatttt ttttttttt ttaaagatta atctgtgtac attataggtg aaaaaatggg      420
ccagaggggt ggattttttt aacatgttaa aaatggggaa cttttttatac ggatcgaatc     480
atcaaaatgg gttgggttca cccgaaacac ttcctctcca atattgtat taataaatag      540
ttgtatgatt acaaacatta aatattttca acaatatttt ttaacaaatt ggcttatgag     600
gtttattgct taacgtttta ctttgggcaa ttttttccgg ttgacccgtt tgactcattt     660
tctctttaac tgcttttaa cccacccatt tgacctttta gaaaaaaaa aaaaaaaaac       720
ataacccgaa tattggtgta tgttaactgc cacctctagt attttaagaa aatctacatt     780
aattttgaaa atgaaacaag ttacttaatt tgaacttgta atcagataca agccgcactc     840
```

| | |
|---|---|
| gggtgcaagg gaaatccatt ggcgtttgat attacagctg cttgtagtgg atttgttttg | 900 |
| ggtctagtct cagcttcgtg ttatatccg | 929 |

<210> SEQ ID NO 40
<211> LENGTH: 982
<212> TYPE: DNA
<213> ORGANISM: Artificial Sequence
<220> FEATURE:
<223> OTHER INFORMATION: Chemically Synthesized

<400> SEQUENCE: 40

| | |
|---|---|
| agctcacaaa gcacttgaga tggcagaggt tgatgctgat gatgtggatc tacttctttt | 60 |
| atgcacatcg accccggatg atctatttgg tagtgctcca caggtattgc ttcaaattct | 120 |
| tgcagaagat agatgttttc aaatgtgcct aaaaaggttt catttttttaa ttttagtggg | 180 |
| atgtcctgag aaaaaaattg ttgcagtatt tatggaatta aaaaagtatt tgtgttgtat | 240 |
| atagaaatat ttgactgcat ataatttttct tgttgaataa ttggcaatga ttttaacatt | 300 |
| tttttttctta tatggtaatc tcaacgcgtt cctgaatttt tgtatgtttc taccggctgt | 360 |
| agactttaga tttctacagt ttgatcatga tccaatttttc aaaagttttt ttttttaaaaa | 420 |
| gattaatctg tgtacattat aggtgaaaaa atgggccgga ggggtggatt cttttaagtt | 480 |
| ttaacatgtt aaatatgggt aacttttttat acggatcgaa acatcaaaat gggttgggtt | 540 |
| cacctgaaac acttcctctc gaaatattct attaataaat agttgtatga ttacaaacat | 600 |
| taaatatttt caacaatatt ttttttaataa attggcttat gaggtttatt gcttaaagtt | 660 |
| tcactttggg tatttttttc cggttgaccc gtttgactca ttttttctttt aactgctttt | 720 |
| taacccaccc atttgacctt ttagaaaaaa aacacataac ccgaatagat cttttcataa | 780 |
| gtaaattggt gtatgtaaac cgccacctct agtattttaa gaaaatctac attaattttg | 840 |
| aaaatgaaac gagttactta atttgaactt gtaatcagat acaagccgca ctcgggtgca | 900 |
| agggaaatcc attggcattt gatattacag ctgcttgtag tggatttgtt ttgggtctag | 960 |
| tctcagcttc gtgttatatc cg | 982 |

<210> SEQ ID NO 41
<211> LENGTH: 983
<212> TYPE: DNA
<213> ORGANISM: Artificial Sequence
<220> FEATURE:
<223> OTHER INFORMATION: Chemically Synthesized -

<400> SEQUENCE: 41

| | |
|---|---|
| agctcacaaa gcacttgaga tggcagaggt tgatgctgat gatgtggatc tacttctttt | 60 |
| atgcacatcg accccggatg atctatttgg tagtgctcca caggtattgc ttcaaattct | 120 |
| tgcagaagat agatgttttc aaatgtgcct aaaaaggttt catttttta attttagtgg | 180 |
| gatgtcctga gaaaaaaatt gttgcagtat ttatggaatt aaaaaagtat ttgtgttgta | 240 |
| tatagaaata tttgactgca tataatttttc ttgttgaata attggcaatg attttaacat | 300 |
| ttttttttctt atatggtaat ctcaacgcgt tcctgaattt ttgtatgttt ctaccggctg | 360 |
| tagactttag atttctacag tttgatcatg atccaatttt caaaagtttt ttttttaaaa | 420 |
| agattaatct gtgtacatta aggtgaaaaa atgggccgg agggggtggat tcttttaagt | 480 |
| tttaacatgt taaatatggg taacttttta tacggatcga acatcaaaa tgggttgggt | 540 |
| tcacccgaaa cacttcctct cgaaatattc tattaataaa tagttgtatg attacaaaca | 600 |
| ttaaatatttt tcaacaatat ttttttaata aattggctta tgaggtttat gcttaaagt | 660 |

```
ttcactttgg gtatttttt  ccggttgacc cgtttgactc atttttctt  taactgcttt    720 ttaacccacc catttgacct tttagaaaaa aaacacataa cccgaataga tcttttcata    780
agtaaattgg tgtatgtaaa ccgccacctc tagtatttta agaaaatcta cattaatttt    840
gaaaatgaaa caagttactt aatttgaact tgtaatcaga tacaagccgc actcgggtgc    900
aagggaaatc cattggcatt tgatattaca gctgcttgta gtggatttgt tttgggtcta    960
gtctcagctt cgtgttatat ccg                                           983
```

LOW SATURATED-FAT SUNFLOWER AND ASSOCIATED METHODS

CROSS-REFERENCE TO RELATED APPLICATION

This application claims the benefit of the filing date of U.S. Provisional Patent Application Ser. No. 61/015,591, filed Dec. 20, 2007. This application is related to application Ser. No. 12/340,558, filed Dec. 19, 2008, pending.

FIELD OF THE INVENTION

The present invention relates to new and distinctive sunflowers producing seeds that are low in saturated fat and, optionally, high in linoleic acid as well as associated methods. The present invention further relates to non-genetically modified, non-mutagenized sunflowers having glyphosate resistance and associated methods.

BACKGROUND OF THE INVENTION

The cultivated sunflower (*Helianthus annuus* L.) is a major worldwide source of vegetable oil. In the United States, approximately 4 million acres are planted in sunflowers annually, primarily in the Dakotas and Minnesota.

The very rapid expansion over the last decade of acreage planted in sunflower in the United States is due in part to several important developments in the field of sunflower breeding and varietal improvement. One significant development was the discovery of cytoplasmic male sterility and genes for fertility restoration, a discovery that allowed the production of hybrid sunflowers. The hybrids thus produced were introduced during the early 1970s.

A description of cytoplasmic male sterility (CMS) and genetic fertility restoration in sunflowers is presented by Fick, "Breeding and Genetics," in *Sunflower Science and Technology* 279-338 (J. F. Carter ed. 1978), the contents of which are incorporated herein by reference.

Sunflower oil is comprised primarily of palmitic (16:0), stearic (18:0), oleic (18:1), linoleic (18:2) and linolenic (18:3) acids. While other unusual fatty acids exist in plants, palmitic, stearic, oleic, linoleic, and linolenic acids comprise about 88% of the fatty acids present in the world production of vegetable oils. (J. L. Harwood, Plant Acyl Lipids: Structure, Distribution and Analysis, 4 *Lipids: Structure and Function*, P. K. Stumpf and E. E. Conn ed. (1988).) Palmitic and stearic acids are saturated fatty acids that have been demonstrated in certain studies to contribute to an increase in the plasma cholesterol level, a factor in coronary heart disease. According to recent studies, vegetable oils high in unsaturated fatty acids, such as oleic and linoleic acids, may have the ability to lower plasma cholesterol. Saturated fatty acids also have higher melting points in general than unsaturated fatty acids of the same carbon number, which contributes to cold tolerance problems in foodstuffs and can contribute to a waxy or greasy feel in the mouth during ingestion. It is also known that food products made from fats and oils having less than about 3% saturated fatty acids will typically contain less than 0.5 gram saturated fat per serving and as a result can be labeled as containing "zero saturated fat" under current labeling regulations. Thus, for a number of reasons, it is desirable to produce a sunflower oil having low levels of palmitic and stearic acids and high levels of oleic or linoleic acids.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior because, for most traits, the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth. The goal of plant breeding is to develop new, unique and superior sunflower cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same sunflower traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is due to the breeder's selection, which occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new sunflower cultivars.

The development of new sunflower cultivars requires the development and selection of sunflower varieties, the crossing of these varieties, and selection of superior hybrid crosses. The hybrid seed is produced by manual crosses between selected male-fertile parents or by using male sterility systems. These hybrids are selected for certain single gene traits such as pod color, flower color, pubescence color, or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, sunflower breeders commonly harvest seeds from each plant in a population and thresh them together to form a bulk. Part of the bulk is used to plant the next generation and part is put in reserve. The procedure has been referred to as modified single-seed descent.

The multiple-seed procedure has been used to save labor at harvest. It is considerably faster to remove seeds with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar can incur additional costs to the seed producer, the grower, processor and consumer due to special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Sunflower, *Helianthus annuus* L., is an important and valuable field crop. Thus, a continuing goal of plant breeders is to develop stable, high yielding sunflower cultivars that are agronomically sound. A current goal is to maximize the amount of grain produced on the land used and to supply food for both animals and humans. To accomplish this goal, the sunflower breeder must select and develop sunflower plants that have traits that result in superior cultivars.

The foregoing examples of the related art and limitations related therewith are intended to be illustrative and not exclusive. Other limitations of the related art will become apparent to those of skill in the art upon a reading of the specification.

BRIEF SUMMARY OF THE INVENTION

The following embodiments are described in conjunction with systems, tools and methods which are meant to be exemplary and illustrative, and not limiting in scope. In various embodiments, one or more of the above-described problems have been reduced or eliminated, while other embodiments are directed to other improvements.

According to the invention, there is provided a novel sunflower plant producing seeds having low saturated fat content. This invention, in part, relates to the seeds of sunflower having low saturated fat content, to the plants or plant parts, of sunflower plants producing seeds having low saturated fat content, and to methods for producing a sunflower plant produced by crossing the sunflower plants producing seeds having low saturated fat content with itself or another sunflower cultivar, and the creation of variants by mutagenesis or transformation of sunflower plants producing seeds having low saturated fat content.

Aspects of the invention provide novel sunflower plants producing seeds having low saturated fat content and high linoleic acid content. This invention, in part, relates to the seeds of sunflower having low saturated fat content and high linoleic acid content, to the plants, or plant parts, of sunflower plants producing seeds having low saturated fat content and high linoleic acid content, and to methods for producing a sunflower plant produced by crossing the sunflower plants producing seeds having low saturated fat content and high linoleic acid content with itself or another sunflower cultivar, and the creation of variants by mutagenesis or transformation of sunflower plants producing seeds having low saturated fat content and high linoleic acid content.

Examples of seeds having low saturated fat content include, but are not limited to, seeds having about 2.8% or less, about 2.9% or less, about 3% or less, about 3.1% or less, about 3.2% or less, or about 3.3% or less total combined palmitic acid (16:0) and stearic acid (18:0) content.

Examples of seeds of having low saturated fat content and high linoleic acid (18:2) content include, but are not limited to, seeds having about 4.1% or less, about 5% or less, about 6% or less, about 7% or less, about 8% or less, about 9% or less, about 10% or less, about 11% or less, or about 12% or less total combined palmitic acids (16:0) and stearic acid (18:0) content and having about 15%, about 20%, about 25%, about 30%, about 35%, about 40%, about 45%, about 50%, about 55%, about 60%, about 65%, about 70%, or about 74% or more linoleic acid (18:2).

Thus, any such methods using the sunflower plants that produce seeds having low saturated fat and, optionally, high linoleic acid content, are part of this invention (e.g., selfing, backcrosses, hybrid production, crosses to populations, and the like). All plants produced using sunflower plants producing seeds having as a parent low saturated fat and, optionally, high linoleic acid content, are within the scope of this invention. Advantageously, the sunflower plant could be used in crosses with other, different, sunflower plants to produce first generation ($F_1$) sunflower hybrid seeds and plants with superior characteristics.

In another aspect, the present invention provides for single or multiple gene converted sunflower plants producing seeds having low saturated fat and, optionally, high linoleic acid content. The transferred gene(s) may preferably be a dominant or recessive allele. The transferred gene(s) can confer such traits as herbicide resistance, insect resistance, resistance for bacterial, fungal, or viral disease, male fertility, male sterility, enhanced nutritional quality, and industrial usage. The gene may be a naturally occurring sunflower gene or a transgene introduced through genetic engineering techniques.

In another aspect, the present invention provides regenerable cells for use in tissue culture of sunflower plants producing seeds having low saturated fat and, optionally, high linoleic acid content. The tissue culture can be capable of regenerating plants having the physiological and morphological characteristics of the foregoing sunflower plant producing seeds having low saturated fat and, optionally, high linoleic acid content, and of regenerating plants having substantially the same genotype as the foregoing sunflower plant. The regenerable cells in such tissue cultures can be embryos, protoplasts, meristematic cells, callus, pollen, leaves, anthers, roots, root tips, flowers, seeds, pods or stems. Still further, the present invention provides sunflower plants regenerated from the tissue cultures of the invention.

In another aspect, the present invention provides a method of introducing a desired trait into sunflower plants producing seeds having low saturated fat and, optionally, high linoleic acid content, wherein the method comprises: crossing a sunflower plant producing seeds having low saturated fat and, optionally, high linoleic acid content with a plant of another sunflower cultivar that comprises a desired trait to produce $F_1$ progeny plants, wherein the desired trait is selected from the group consisting of male sterility, herbicide resistance, insect resistance, and resistance to bacterial disease, fungal disease or viral disease; selecting one or more progeny plants that have the desired trait to produce selected progeny plants; crossing the selected progeny plants with the sunflower plants producing seeds having low saturated fat and, optionally, high linoleic acid content to produce backcross progeny plants; selecting for backcross progeny plants that have the desired trait and physiological and morphological characteristics of sunflower plants producing seeds having low saturated fat and, optionally, high linoleic acid content to produce selected backcross progeny plants; and repeating these steps to produce selected first or higher backcross progeny plants that comprise the desired trait and all of the physiological and morphological characteristics of sunflower plants producing seeds having low saturated fat and, optionally, high linoleic acid content.

In addition to the exemplary aspects and embodiments described above, further aspects and embodiments will become apparent by study of the following descriptions.

BRIEF DESCRIPTION OF THE DRAWINGS

FIG. 2 shows alignment of sequences of the KASII-2 gene from the two parental lines showing SNPs and indels (IDs numbers 333.1 (SEQ ID NO:38) and 333.2 (SEQ ID NO:39) represented clones from OND163R amplicons, and 332.4 (SEQ ID NO:40) and 332.5 (SEQ ID NO:41) from H280R [1]/687R-1-8-1 amplicons);

FIG. 3 shows co-localization of the low palmitic acid QTL (Panel A) and fatty acid gene KASIII-2 (Panel B) on LG 5.

DETAILED DESCRIPTION OF THE INVENTION

Figure 1:
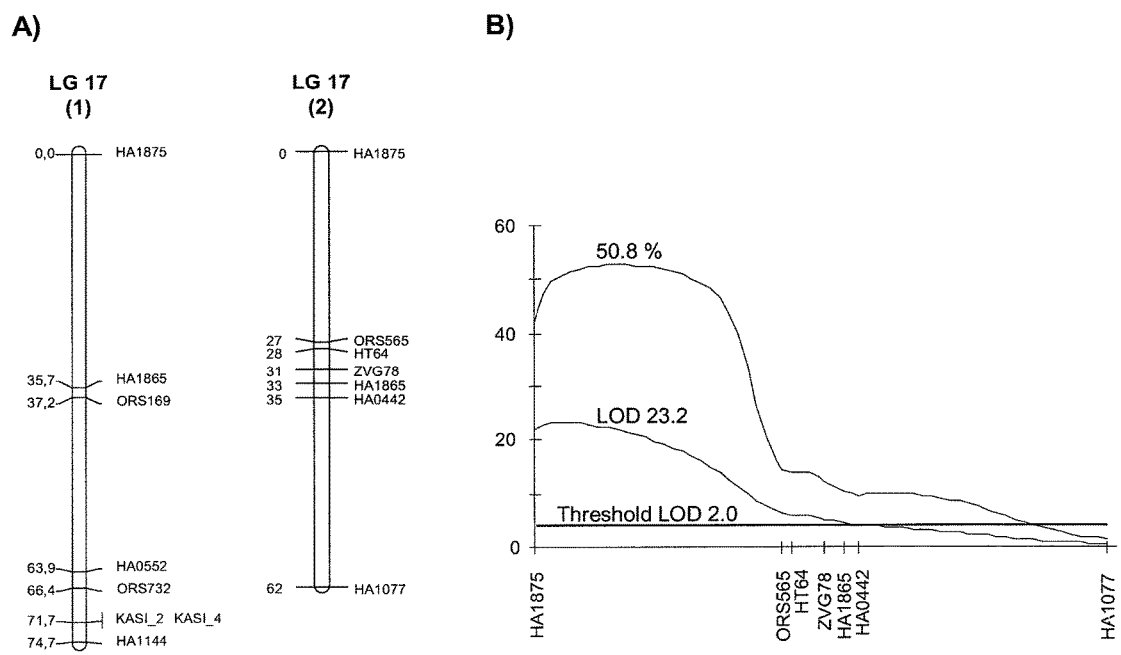
FIG. 1 shows fine mapping of the low stearic acid QTL in the HA1875-HA1865 interval of LG17 (Panel A: Maps of LG 17 with new markers (in blue color) and Panel B: Fine mapping of the low stearic acid QTL to the HA1875-ORS565 interval)

In the description and tables which follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Elite sunflower. A sunflower cultivar which has been stabilized for certain commercially important agronomic traits comprising a stabilized yield of about 100% or greater relative to the yield of check varieties in the same growing location growing at the same time and under the same conditions. In one embodiment, "elite sunflower" means a sunflower cultivar stabilized for certain commercially important agronomic traits comprising a stabilized yield of 110% or greater relative to the yield of check varieties in the same growing location growing at the same time and under the same conditions. In another embodiment, "elite sunflower" means a sunflower cultivar stabilized for certain commercially important agronomic traits comprising a stabilized yield of 115% or greater relative to the yield of check varieties in the same growing location growing at the same time and under the same conditions.

Embryo. The embryo is the small plant contained within a mature seed.

FAME analysis. Fatty Acid Methyl Ester analysis is a method that allows for accurate quantification of the fatty acids that make up complex lipid classes.

Imidazolinone resistance (Imi). Resistance and/or tolerance is conferred by one or more genes which alter acetolactate synthase (ALS), also known as acetohydroxy acid synthase (AHAS) allowing the enzyme to resist the action of imidazolinone.

Mutagenesis. Mutagenesis refers to mutagenesis of a plant or plant part with a mutagen (e.g., a chemical or physical agent that increases the frequency of mutations in a target plant or plant part). By way of non-limiting example, the double chemical mutagenesis technique of Konzak, as described in U.S. Pat. No. 6,696,294 (the disclosure of which is incorporated by reference herein), can be used to induce mutant alleles in endogenous plant genes.

Oil content. This is measured as percent of the whole dried seed and is characteristic of different varieties. It can be determined using various analytical techniques such as NMR, NIR, and Soxhlet extraction.

Percentage of total fatty acids. This is determined by extracting a sample of oil from seed, producing the methyl esters of fatty acids present in that oil sample and analyzing the proportions of the various fatty acids in the sample using gas chromatography. The fatty acid composition can also be a distinguishing characteristic of a variety.

Single Gene Converted (Conversion). Single gene converted (conversion) plant refers to plants which are developed by a plant breeding technique called backcrossing, or via genetic engineering, wherein essentially all of the desired morphological and physiological characteristics of a variety are recovered in addition to the single gene transferred into the variety via the backcrossing technique or via genetic engineering.

Stabilized. Reproducibly passed from one generation to the next generation of inbred plants of same variety.

Total Saturated (TOTSAT). Total percent oil of the seed of the saturated fats in the oil including C12:0, C14:0, C16:0, C18:0, C20:0, C22:0 and C24:0.

According to a particular embodiment the invention, there is provided a novel sunflower plant producing seeds having low saturated fat content. This embodiment relates to the seeds of sunflower having low saturated fat content, to the plants, or plant parts, of sunflower plants producing seeds having low saturated fat content, and to methods for producing a sunflower plant produced by crossing the sunflower plant producing seeds having low saturated fat content with itself or another sunflower cultivar, and the creation of variants by mutagenesis or transformation of sunflower plants producing seeds having low saturated fat content.

Other aspects of the invention provide novel sunflower plants producing seeds having low saturated fat content and high linoleic acid content. This embodiment relates to the seeds of sunflower having low saturated fat content and high linoleic acid content, to the plants, or plant parts, of sunflower plants producing seeds having low saturated fat content and high linoleic acid content, and to methods for producing a sunflower plant produced by crossing the sunflower plants producing seeds having low saturated fat content and high linoleic acid content with itself or another sunflower cultivar, and the creation of variants by mutagenesis or transformation of sunflower plants producing seeds having low saturated fat content and high linoleic acid content.

Examples of seeds having low saturated fat content include, but are not limited to, seeds having about 2.8% or less, about 2.9% or less, about 3% or less, about 3.1% or less, about 3.2% or less, or about 3.3% or less total combined palmitic acid (16:0) and stearic acid (18:0) content.

Examples of seeds of having low saturated fat content and high linoleic acid (18:2) content include, but are not limited to, seeds having about 6% or less, about 4.1% or less, about 5% or less, about 6% or less, about 7% or less, about 8% or less, about 9% or less, about 10% or less, about 11% or less, or about 12% or less total combined palmitic acids (16:0) and stearic acid (18:0) content and having about 15%, about 20%, about 25%, about 30%, about 35%, about 40%, about 45%, about 50%, about 55%, about 60%, about 65%, about 70%, or about 74% or more linoleic acid (18:2).

Thus, any such methods using the sunflower plants producing seeds having low saturated fat and, optionally, high linoleic acid content, are part of this invention (e.g., selfing, backcrosses, hybrid production, crosses to populations, and the like). All plants produced using sunflower plants that produce seeds having as a parent low saturated fat and, optionally, high linoleic acid content, are within the scope of this invention. Advantageously, the sunflower plant could be used in crosses with other, different, sunflower plants to produce first generation ($F_1$) sunflower hybrid seeds and plants with superior characteristics.

In another aspect, the present invention provides for single or multiple gene converted sunflower plants producing seeds having low saturated fat and, optionally, high linoleic acid content. The transferred gene(s) may preferably be a dominant or recessive allele. Preferably, the transferred gene(s) will confer such traits as herbicide resistance, insect resistance, bacterial resistance, fungal resistance, viral disease resistance, male fertility, male sterility, enhanced nutritional quality, and industrial usage. The gene may be a naturally occurring sunflower gene or a transgene introduced through genetic engineering techniques.

In another aspect, the present invention provides regenerable cells for use in tissue culture of sunflower plants producing seeds having low saturated fat and, optionally, high linoleic acid content. The tissue culture will preferably be capable of regenerating plants having the physiological and morphological characteristics of the foregoing sunflower plant producing seeds having low saturated fat and, optionally, high linoleic acid content, and of regenerating plants having substantially the same genotype as the foregoing sunflower plant. The regenerable cells in such tissue cultures can be embryos, protoplasts, meristematic cells, callus, pollen, leaves, anthers, roots, root tips, flowers, seeds, pods or stems. Still further, an embodiment of the invention provides sunflower plants regenerated from the tissue cultures of the invention.

In another aspect, the present invention provides a method of introducing a desired trait into sunflower plants producing seeds having low saturated fat and, optionally, high linoleic acid content, wherein the method comprises: crossing a sunflower plant that produces seeds having low saturated fat and, optionally, high linoleic acid content with a plant of another sunflower cultivar that comprises a desired trait to produce $F_1$ progeny plants, wherein the desired trait is selected from the group consisting of male sterility, herbicide resistance, insect resistance, and resistance to bacterial disease, fungal disease or viral disease; selecting one or more progeny plants that have the desired trait to produce selected progeny plants; crossing the selected progeny plants with the sunflower plants producing seeds having low saturated fat and, optionally, high linoleic acid content to produce backcross progeny plants; selecting for backcross progeny plants that have the desired trait and physiological and morphological characteristics of sunflower plants that produce seeds having low saturated fat and, optionally, high linoleic acid content to produce elected backcross progeny plants; and repeating these steps to produce selected first or higher backcross progeny plants that comprise the desired trait and all of the physiological and morphological characteristics of sunflower plants producing seeds having low saturated fat and, optionally, high linoleic acid content.

Useful methods include, but are not limited to, expression vectors introduced into plant tissues using a direct gene transfer method such as microprojectile-mediated delivery, DNA injection, electroporation and the like. Expression vectors can be introduced into plant tissues using the microprojectile media delivery with the biolistic device *Agrobacterium*-mediated transformation. Transformant plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional or modified versions of native or endogenous genes (perhaps driven by different promoters) in order to alter the traits of a plant in a specific manner. Such foreign additional and/or modified genes are referred to herein collectively as "transgenes." Over the last fifteen to twenty years, several methods for producing transgenic plants have been developed and the present invention, in particular embodiments, also relates to transformed versions of the claimed variety or cultivar.

Plant transformation involves the construction of an expression vector which will function in plant cells. Such a vector comprises DNA that includes a gene under control of or operatively linked to a regulatory element (for example, a promoter). The expression vector may contain one or more such operably linked gene/regulatory element combinations.

The vector(s) may be in the form of a plasmid and can be used alone or in combination with other plasmids to provide transformed sunflower plants using transformation methods as described below to incorporate transgenes into the genetic material of the sunflower plant(s).

Expression Vectors for Sunflower Transformation: Marker Genes

Expression vectors include at least one genetic marker, operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many commonly used selectable marker genes for plant transformation are well known in the transformation arts and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene under the control of plant regulatory signals, which confers resistance to kanamycin. See, e.g., Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. See, e.g., Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase and the bleomycin resistance determinant. See Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. See Comai et al., *Nature* 317:741-744 (1985); Gordon-Kamm et al., *Plant Cell* 2:603-618 (1990); and Stalker et al., *Science* 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. See Eichholtz et al., *Somatic Cell Mol. Genet.* 13:67 (1987); Shah et al., *Science* 233:478 (1986); Charest et al., *Plant Cell Rep.* 8:643 (1990).

Another class of marker genes for plant transformation requires screening of presumptively transformed plant cells rather than direct genetic selection of transformed cells for resistance to a toxic substance, such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. See, R. A. Jefferson, *Plant Mol. Biol. Rep.* 5:387 (1987); Teeri et al., *EMBO J.* 8:343 (1989); Koncz et al., *Proc. Natl. Acad. Sci. U.S.A.* 84:131 (1987); DeBlock et al., *EMBO J.* 3:1681 (1984).

Recently, in vivo methods for visualizing GUS activity that do not require destruction of plant tissue have been made available. Molecular Probes publication 2908, *Ima-* gene, T. M. Green, p. 1-4 (1993); and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. See, Chalfie et al., *Science* 263:802 (1994). GFP and mutants of GFP may be used as screenable markers.

Expression Vectors for Sunflower Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA that is upstream from the start of transcription and that is involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in sunflower. Optionally, the inducible promoter is operably linked to a nucleotide sequence encoding a signal sequence which is operably linked to a gene for expression in sunflower. With an inducible promoter, the rate of transcription increases in response to an inducing agent.

Any inducible promoter can be used in the instant invention. See, Ward et al., *Plant Mol. Biol.* 22:361-366 (1993). Exemplary inducible promoters include, but are not limited to: those from the ACEI system that responds to copper (Mett et al., *PNAS* 90:4567-4571 (1993)); In2 gene from maize that responds to benzenesulfonamide herbicide safeners (Hershey et al., *Mol. Gen. Genetics* 227:229-237 (1991); and Gatz et al., *Mol. Gen. Genetics* 243:32-38 (1994)); and Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in sunflower or the constitutive promoter is operably linked to a nucleotide sequence encoding a signal sequence which is operably linked to a gene for expression in sunflower.

Different constitutive promoters can be utilized in the instant invention. Exemplary constitutive promoters include, but are not limited to: the promoters from plant viruses such as the 35S promoter from CaMV (Odell et al., *Nature* 313:810-812 (1985)); the promoters from rice actin genes (McElroy et al., *Plant Cell* 2:163-171 (1990)); ubiquitin (Christensen et al., *Plant Mol. Biol.* 12:619-632 (1989), and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); and maize H3 histone (Lepetit et al., *Mol. Gen. Genetics* 231: 276-285 (1992), and Atanassova et al., *Plant Journal* 2 (3):291-300 (1992)). The ALS promoter, Xba1/NcoI fragment 5' to the *Brassica napus* ALS3 structural gene (or a nucleotide sequence similarity to the Xba1/NcoI fragment), represents a particularly useful constitutive promoter. See PCT application WO 96/30530.

C. Tissue-Specific or Tissue-Preferred Promoters

A tissue-specific promoter is operably linked to a gene for expression in sunflower. Optionally, the tissue-specific promoter is operably linked to a nucleotide sequence encoding a signal sequence which is operably linked to a gene for expression in sunflower. Plants transformed with a gene of interest operably linked to a tissue-specific promoter can produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983), and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985), and Timko et al., *Nature* 318:579-582 (1985)); an another-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Transport of protein produced by transgenes to a subcellular compartment, such as the chloroplast, vacuole, peroxisome, glyoxysome, cell wall or mitochondrion or for secretion into the apoplast, can be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment, or for secretion to the apoplast. Many signal sequences are known in the art. See, e.g., Becker et al., *Plant Mol. Biol.* 20:49 (1992); P. S. Close, Master's Thesis, Iowa State University (1993); C. Knox et al., "Structure and Organization of Two Divergent Alpha-Amylase Genes from Barley," *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., A short amino acid sequence able to specify nuclear location, *Cell* 39:499-

509 (1984); Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

In aspects of the invention, the transgenic plant provided for commercial production of foreign protein is a sunflower plant. In other aspects, the biomass of interest is seed. For the relatively small number of transgenic plants that show higher levels of expression, a genetic map can be generated primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques.

Likewise, agronomic genes can be expressed in transformed plants. More particularly, plants can be genetically engineered to express various phenotypes of agronomic interest. Exemplary genes that may be used in this regard include, but are not limited to, those categorized below.

1. Genes that Confer Resistance to Pests or Disease and that Encode:

A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, e.g., Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (Arabidopsis RSP2 gene for resistance to *Pseudomonas syringae*).

B) A gene conferring resistance to a pest, such as soybean cyst nematode. See, e.g., PCT Application WO 96/30517; PCT Application WO 93/19181.

C) A *Bacillus thuringiensis* protein, a derivative thereof or a synthetic polypeptide modeled thereon. See, e.g., Geiser et al., *Gene* 48:109 (1986), which discloses the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D) A lectin. See, for example, the disclosure by Van Damme et al., *Plant Molec. Biol.* 24:25 (1994), who disclose the nucleotide sequences of several *Clivia miniata* mannose-binding lectin genes.

E) A vitamin-binding protein such as avidin. See PCT application US93/06487. The application teaches the use of avidin and avidin homologues as larvicides against insect pests.

F) An enzyme inhibitor, for example, a protease or proteinase inhibitor or an amylase inhibitor. See, e.g., Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor I); Sumitani et al., *Biosci. Biotech. Biochem.* 57:1243 (1993) (nucleotide sequence of *Streptomyces nitrosporeus* .alpha.-amylase inhibitor); and U.S. Pat. No. 5,494,813 (Hepher and Atkinson, issued Feb. 27, 1996).

G) An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H) An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., which discloses genes encoding insect-specific, paralytic neurotoxins.

I) An insect-specific venom produced in nature by a snake, a wasp, etc. For example, see Pang et al., *Gene* 116:165 (1992), for disclosure of heterologous expression in plants of a gene coding for a scorpion insectotoxic peptide.

J) An enzyme responsible for a hyperaccumulation of a monoterpene, a sesquiterpene, a steroid, hydroxamic acid, a phenylpropanoid derivative or another non-protein molecule with insecticidal activity.

K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

L) A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M) A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N) A membrane permease, a channel former or a channel blocker. For example, see the disclosure of Jaynes et al., *Plant Sci.* 89:43 (1993), of heterologous expression of a cecropin-β lytic peptide analog to render transgenic tobacco plants resistant to *Pseudomonas solanacearum*.

O) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q) A virus-specific antibody. See, for example, Tavladoraki et al., *Nature* 366:469 (1993), who show that transgenic plants expressing recombinant antibody genes are protected from virus attack.

R) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S) A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide:

A) An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B) An herbicide that inhibits photosynthesis, such as a triazine (psbA and gs+ genes) or a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A) Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B) Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which is responsible for maize mutants characterized by low levels of phytic acid. See Raboy et al., *Maydica* 35:383 (1990).

C) Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene); Steinmetz et al., *Mol. Gen. Genet.* 20:220 (1985) (nucleotide sequence of *Bacillus subtilis* levansucrase gene); Pen et al., *Bio/Technology* 10:292 (1992) (production of transgenic plants that express *Bacillus lichenifonnis* α-amylase); Elliot et al., *Plant Molec. Biol.* 21:515 (1993) (nucleotide sequences of tomato invertase genes); Sogaard et al., *J. Biol. Chem.* 268:22480 (1993) (site-directed mutagenesis of barley α-amylase gene); and Fisher et al., *Plant Physiol.* 102:1045 (1993) (maize endosperm starch branching enzyme II).

Methods for Sunflower Transformation

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, B. R. Glick and J. E. Thompson, Eds. (CRC Press, Inc., Boca Raton, 1993) pages 67-88. In addition, expression vectors and in vitro culture methods for plant cell or tissue transformation and regeneration of plants are available. See, e.g., Gruber et al., "Vectors for Plant Transformation" in *Methods in Plant Molecular Biology and Biotechnology*, B. R. Glick and J. E. Thompson, Eds. (CRC Press, Inc., Boca Raton, 1993) pages 89-119.

A) *Agrobacterium*-mediated Transformation—One method for introducing an expression vector into plants is based on the natural transformation system of *Agrobacterium*. See, e.g., Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, C. I. Kado, *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B) Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); J. C. Sanford, *Trends Biotech.* 6:299 (1988); Klein et al., *Bio/*

*Technology* 6:559-563 (1988); J. C. Sanford, *Physiol. Plant* 7:206 (1990); Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.* 4:2731 (1985); Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985), and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992), and Spencer et al., *Plant Mol. Biol.* 24:51-61 (1994).

Following transformation of sunflower target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety can then be crossed, with another (non-transformed or transformed) variety, in order to produce a new transgenic variety. Alternatively, a genetic trait which has been engineered into a particular sunflower cultivar using the foregoing transformation techniques can be moved into another cultivar using traditional backcrossing techniques that are well known in the plant breeding arts. For example, a backcrossing approach can be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of Sunflowers

Further production of a sunflower plant producing seeds having low saturated fat and, optionally, high linoleic acid content can occur by self-pollination or by tissue culture and regeneration. Tissue culture of various tissues of sunflower and regeneration of plants therefrom is known. For example, the propagation of a sunflower cultivar by tissue culture is described in U.S. Pat. No. 6,998,516.

Further reproduction of the variety can occur by tissue culture and regeneration. Tissue culture of various tissues of soybeans and regeneration of plants therefrom is well known and widely published. For example, reference may be had to U.S. Pat. No. 6,998,516, which is incorporated herein in its entirety by reference. Thus, another aspect of this invention is to provide cells, which upon growth and differentiation, produce a sunflower plants having seeds containing low saturated fat and, optionally, high linoleic acid content.

As used herein, the term "tissue culture" indicates a composition comprising isolated cells of the same or a different type, or a collection of such cells organized into parts of a plant. Exemplary types of tissue cultures include protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185, 5,973,234 5,977,445, and 6,998,516 describe certain techniques, the disclosures of which are incorporated herein by reference.

Single-Gene Converted (Conversion) Plants

When the term "sunflower plant" is used in the context of the present invention, this also includes any single gene conversions of that variety. The term "single gene converted plant" as used herein refers to those sunflower plants which are developed by a plant breeding technique called backcrossing, or via genetic engineering, wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent (i.e., backcrossing 1, 2, 3, 4, 5, 6, 7, 8 or more times to the recurrent parent). The parental sunflower plant, which contributes the gene for the desired characteristic, is termed the "nonrecurrent" or "donor parent." This terminology refers to the fact that the nonrecurrent parent is used one time in the backcross protocol and therefore does not recur. The parental sunflower plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a sunflower plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic and, therefore, the desired physiological and morphological constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are hereby incorporated by reference.

This invention also is directed to methods for producing a sunflower plant by crossing a first parent sunflower plant with a second parent sunflower plant, wherein the first or second parent sunflower plant is a sunflower plant producing seeds having low saturated fat and, optionally, high linoleic acid content. Further, both first and second parent sunflower plants can originate from a sunflower plant producing seeds having low saturated fat and, optionally, high linoleic acid content. Thus, any such methods using a sunflower plant producing seeds having low saturated fat and, optionally, high linoleic acid content are part of this invention (i.e., selling, backcrosses, hybrid production, crosses to populations, and the like). All plants produced using a sunflower plant producing seeds having low saturated fat and, optionally, high linoleic acid content as a parent are within the scope of this invention, including those developed from varieties derived from a sunflower plant producing seeds having low saturated fat and, optionally, high linoleic acid content. Advantageously, the sunflower variety could be used in crosses with other, different, sunflower plants to produce first generation ($F_1$) sunflower hybrid seeds and plants with superior characteristics. The variety of the invention can also be used for transformation where exogenous genes are introduced and expressed by the variety of the invention. Genetic variants created either through traditional breeding methods using a sunflower plant producing seeds having low saturated fat and, optionally, high linoleic acid content or through transformation of a sunflower plant producing seeds having low saturated fat and, optionally, high linoleic acid content by any of a number of protocols known to those of skill in the art are intended to be within the scope of this invention.

EXAMPLES

The present invention is further described in the following examples, which are offered by way of illustration and are not intended to limit the invention in any manner.

Example 1: Sunflowers Producing Seeds Having Low Saturated Fat Content

Sunflower germplasm with unusually low saturate levels has been developed through normal breeding techniques. Seed oil content of sunflower cultivars are provided in Table 1.

TABLE 1

| Sample | C16:0 | C16:1 | C18:0 | C18:1 | C18:2 | TOTAL SATS | C16:0 + C18:0 |
|---|---|---|---|---|---|---|---|
| H757B/LS10670B-B-17-3-23.06 | 2.34 | 0.09 | 0.48 | 94.18 | 1.51 | 3.39 | 2.82 |
| H757B/LS10670B-B-17-3-33.11 | 2.47 | 0.11 | 0.51 | 93.62 | 2.11 | 3.42 | 2.98 |
| H757B/LS10670B-B-17-3-23.04 | 2.24 | 0.09 | 0.53 | 94.25 | 1.49 | 3.45 | 2.77 |
| H757B/LS10670B-B-17-3-02.08 | 2.70 | 0.13 | 0.50 | 93.26 | 2.24 | 3.67 | 3.2 |
| H757B/LS10670B-B-17-3-18.21 | 2.45 | 0.11 | 0.54 | 93.62 | 1.73 | 3.68 | 2.99 |
| HE06EE010716.001 | 2.17 | 0.11 | 0.82 | 94.29 | 1.41 | 3.63 | 2.99 |
| HE06EE010834.002 | 2.31 | 0.11 | 0.65 | 94.74 | 0.82 | 3.68 | 2.95 |
| HE06EE010746.002 | 2.40 | 0.11 | 0.72 | 93.87 | 1.03 | 3.68 | 3.12 |
| HE06EE010700.003 | 2.48 | 0.13 | 0.57 | 93.46 | 1.78 | 3.78 | 3.05 |
| HE06EE016032.005 | 2.42 | 0.10 | 0.64 | 92.86 | 1.82 | 3.82 | 3.06 |
| HE06EE016037.005 | 2.25 | 0.08 | 0.75 | 93.06 | 1.71 | 3.86 | 3.00 |
| HE06EE016032.002 | 2.40 | 0.10 | 0.70 | 93.00 | 1.72 | 3.87 | 3.09 |
| HE06EE010717.002 | 2.44 | 0.10 | 0.82 | 89.76 | 5.51 | 3.88 | 3.26 |
| HE06EE010695.001 | 2.48 | 0.12 | 0.66 | 91.93 | 3.20 | 3.88 | 3.14 |
| HE06EE010816.002 | 2.34 | 0.12 | 0.88 | 94.10 | 1.24 | 3.88 | 3.22 |
| HE06EE010700.001 | 2.48 | 0.14 | 0.65 | 94.31 | 0.89 | 3.90 | 3.13 |
| HE06EE010814.002 | 2.46 | 0.10 | 0.79 | 94.11 | 1.19 | 3.91 | 3.24 |
| HE06EE010760.004 | 2.54 | 0.11 | 0.63 | 94.07 | 1.16 | 3.92 | 3.16 |
| HE06EE010741.003 | 2.34 | 0.11 | 0.93 | 94.51 | 0.73 | 3.93 | 3.26 |
| HE06EE010737.003 | 2.33 | 0.13 | 0.96 | 93.53 | 1.12 | 3.93 | 3.29 |
| HE06EE016050.005 | 2.41 | 0.08 | 0.73 | 92.57 | 2.67 | 3.94 | 3.13 |
| HE06EE016032.004 | 2.44 | 0.11 | 0.63 | 92.49 | 1.80 | 3.94 | 3.07 |
| HE06EE010763.002 | 2.43 | 0.11 | 0.78 | 94.28 | 0.98 | 3.94 | 3.21 |
| HE06EE010829.002 | 2.53 | 0.13 | 0.70 | 93.26 | 1.84 | 3.95 | 3.23 |
| HE06EE010738.002 | 2.78 | 0.15 | 0.62 | 89.75 | 5.22 | 3.96 | 3.40 |
| HE06EE010741.004 | 2.42 | 0.11 | 0.88 | 94.10 | 0.61 | 3.96 | 3.30 |
| HE06EE010824.004 | 2.35 | 0.10 | 0.80 | 94.14 | 1.15 | 3.97 | 3.15 |
| HE06EE010745.003 | 2.81 | 0.11 | 0.68 | 88.66 | 6.32 | 3.98 | 3.48 |
| HE06EE010816.001 | 2.52 | 0.11 | 0.80 | 91.45 | 3.77 | 3.98 | 3.32 |

Example 2: Sunflowers Producing Seeds Having Low Saturated Fat Content and High Linoleic Acid Content Sunflower germplasm with unusually low saturate levels has been developed through normal breeding techniques. Seed oil content of sunflower cultivars are provided in Table 2.

TABLE 2

| Sample | C16:0 | C16:1 | C18:0 | C18:1 | C18:2 | TOTAL SATS | C16:0 + C18:0 |
|---|---|---|---|---|---|---|---|
| H757B/LS10670B-B-17-3-14.01 | 4.25 | 0.09 | 1.13 | 37.87 | 55.45 | 5.90 | 5.38 |
| H757B/LS10670B-B-17-3-02.18 | 4.80 | 0.11 | 0.68 | 39.63 | 53.55 | 6.05 | 5.48 |
| H757B/LS10670B-B-17-3-27.12 | 4.01 | 0.08 | 1.37 | 38.48 | 54.68 | 6.07 | 5.38 |
| H757B/LS10670B-B-17-3-16.02 | 5.19 | 0.14 | 0.73 | 35.14 | 57.79 | 6.22 | 5.92 |
| H757B/LS10670B-B-17-3-36.22 | 4.99 | 0.09 | 1.25 | 17.97 | 74.37 | 6.81 | 6.24 |

Example 3: Sunflowers Producing Seeds Having Low Saturated Fat Content

Sunflower germplasm with unusually low saturate levels has been developed through normal breeding techniques. Seed oil content of sunflower cultivars are provided in Table 3.

TABLE 3

| Sample | C16:0 | C16:1 | C18:0 | C18:1 | C18:2 | TOTAL SATS |
|---|---|---|---|---|---|---|
| NuSun/No Saturate | | | | | | |
| NS1982.16/OND163R-1-05 | 2.29 | 0.05 | 0.65 | 67.37 | 28.19 | 3.48 |
| NS1982.8 | 2.09 | 0.08 | 0.55 | 79.40 | 15.99 | 3.10 |
| No Saturate/High Oleic | | | | | | |
| NS1982.8-03 | 1.60 | 0.03 | 0.37 | 95.13 | 1.48 | 2.33 |
| NS1982.8 | 1.63 | 0.07 | 0.41 | 94.81 | 1.26 | 2.48 |
| H117R[4]//H757B/LS10670B///NS1982.6-2-023-1-12-076 | 1.79 | 0.05 | 0.29 | 95.30 | 0.84 | 2.57 |
| Low Saturate/Linoleic | | | | | | |
| CND117R/NS1982.8-3-06 | 5.29 | 0.07 | 0.73 | 18.19 | 74.43 | 6.41 |
| OI1601B[2]//H757B/LS10670B[1]///NS1982.6 = B-3-04 | 3.76 | 0.07 | 0.80 | 34.97 | 58.62 | 5.29 |
| CN2343B/4/CN2343B[2]//H757B/LS10670B///NS1982.11#1-3-11 | 3.13 | 0.02 | 2.07 | 36.03 | 56.65 | 6.23 |
| Low Stearic | | | | | | |
| NS1982.8/OND163R-2-12-009 | 2.75 | 0.66 | 0.25 | 92.95 | 1.99 | 3.43 |
| H117R[4]//H757B/LS10670B///NS1982.6-2-023-1-12-038 | 1.90 | 0.04 | 0.27 | 95.03 | 1.00 | 2.65 |
| OID263R/NS1982.8-4-12-002 | 3.08 | 0.12 | 0.27 | 93.54 | 1.48 | 3.87 |
| Low Palmitic | | | | | | |
| H251B[2]/IAST-4 = 1 = 100//NS1982.16-11-39-041 | 1.47 | 0.24 | 2.59 | 92.59 | 0.65 | 5.42 |
| NS1982.14-08 | 1.51 | 0.02 | 2.24 | 92.84 | 1.35 | 4.90 |
| NS1982.16 | 1.52 | 0.06 | 1.05 | 94.37 | 0.85 | 3.39 |
| Very High Oleic | | | | | | |
| H117R[4]//H757B/LS10670B//NS1982.6-2-023-1-12-076 | 1.79 | 0.05 | 0.29 | 95.30 | 0.84 | 2.57 |
| NS1982.8/OND163R-2-12-059 | 1.87 | 0.10 | 0.44 | 95.22 | 0.97 | 2.76 |
| ON3351B/NS1982.8-1-04 | 2.04 | 0.03 | 0.50 | 95.20 | 0.70 | 3.08 |

As can be seen in Table 3, the data demonstrates seed oil having total saturates as low as 2.33% in a high oleic (>80%) background, no Saturate (<3.5%) profile in a NuSun (55-50% oleic) background, oleic levels up to 95.30%; stearic levels as low as 0.25%, palmitic levels as low as 1.47%, and low Saturate (<7.0%) profile in a linoleic (<55% oleic) background.

Example 4: Sunflowers Producing Seeds Having Low Saturated Fat, Stearic Acid, and Palmitic Acid Content Sunflower germplasm with unusually low saturate levels has been developed through normal breeding techniques. Seed oil content of sunflower cultivars are provided in Table 4.

sequences from the parental lines. Nucleotide polymorphisms at the sequence level were developed into markers based on their polymorphic nature and were then screened in the mapping populations. JoinMap 3.0 (Van Ooijen, 2004a) was employed to map the newly developed markers, and MapQTL 5 (Van Ooijen, 2004b) was used to fine map QTLs.

A) Marker Development for Low Stearic Acid

SSR marker development: Eight SSR markers were screened for polymorphisms between parental lines ONN687R and H757B/LS10760B-B-17-3-23-5 of the ONN687R×H757B/LS10760B-B-17-3-23-5 mapping population which was previously used to map the target low stearic acid QTL. (See Table 5.) Four SSR markers, HA0442, CRT22, ORS565 and ORS732, were polymorphic. HA0442 and CRT22 amplicons from ONN687R and H757B/LS10760B-B-17-3-23-5 were resolved on ABI 3730

TABLE 4

| Name | C16:0 | C16:1 | C18:0 | C18:1 | C18:2 | C18:3 | C20:0 | C20:1 | C20:2 | C22:0 | C22:1 | C24:0 | C24:1 | TSats |
|---|---|---|---|---|---|---|---|---|---|---|---|---|---|---|
| NS1982.8/OND163R-12-90 | 1.37 | 0.01 | 1.70 | 91.93 | 2.83 | 0.08 | 0.21 | 0.60 | nd | 0.70 | 0.01 | 0.33 | nd | 4.32 |
| H117R[4]//H757B/LS10670B-B-17-3-23 = B1 = 2 = 16///NS1982.6-2-23.1-1 | 1.39 | 0.02 | 0.53 | 94.89 | 1.55 | 0.08 | 0.09 | 0.66 | nd | 0.40 | 0.03 | 0.19 | nd | 2.60 |
| H117R[4]//H757B/LS10670B-B-17-3-23 = B1 = 2 = 16///NS1982.6-2-23.1-1 | 1.44 | 0.03 | 0.36 | 94.83 | 1.84 | 0.09 | 0.08 | 0.74 | nd | 0.31 | 0.02 | 0.14 | nd | 2.33 |
| H117R[4]//H757B/LS10670B-B-17-3-23 = B1 = 2 = 16///NS1982.6-2-23.1-1 | 1.58 | 0.02 | 0.24 | 94.54 | 2.05 | 0.10 | 0.06 | 0.79 | nd | 0.24 | 0.04 | 0.15 | nd | 2.28 |
| H117R[4]//H757B/LS10670B-B-17-3-23 = B1 = 2 = 16///NS1982.6-2-23.1-1 | 1.89 | 0.03 | 0.24 | 94.17 | 2.31 | 0.13 | 0.04 | 0.70 | nd | 0.21 | 0.03 | 0.11 | nd | 2.50 |
| H117R[4]//H757B/LS10670B-B-17-3-23 = B1 = 2 = 16///NS1982.6-2-23.1-1 | 1.94 | 0.03 | 0.23 | 94.58 | 1.80 | 0.12 | 0.07 | 0.69 | nd | 0.22 | 0.03 | 0.13 | nd | 2.60 |

As can be seen in Table 4, this set of data includes the low values for stearic (0.23%), palmitic (1.37%), and total saturated oils (2.28%).

Example 5: Marker Development for Low Stearic and Low Palmitic

A strategy for marker development was developed as described herein. First, markers from the target QTL regions, developed at Dow AgroSciences as well as from the public resources, were identified and screened for polymorphisms between the parental lines of corresponding mapping populations. Polymorphic markers were then screened in the mapping populations. For monomorphic (non-informative) markers, primers were designed to amplify their corresponding genomic loci and the amplicons were sequenced to identify single nucleotide polymorphisms (SNPs), if any, between the parental lines. TaqMan MGB Allelic Discrimination assays were developed for the identified SNPs and were mapped on the respective population. Second, based on sequences of candidate genes for fatty acids, primers flanking introns were designed to isolate fatty acid gene sequencer, and were 163 bp and 165 bp, respectively, for marker HA0442, and 290 bp and 261 bp, respectively, for CRT22. ORS565 and ORS732 amplicons from ONN687R and H757B/LS10760B-B-17-3-23-5 were resolved on 3% Metaphor gels. The corresponding mapping population ONN687R×H757B/LS10760B-B-17-3-23-5 was genotyped with HA0442, CRT22, ORS565 and ORS732 using the following PCR primers and reaction conditions.

```
HA0442 Forward Primer:
                                    (SEQ ID NO:1)
5'-HEX-TGGAACTGTAAATGGACCCAAG-3'

HA0442 Reverse Primer:
                                    (SEQ ID NO:2)
5'-GCACTGCACCATTTATGAGAAG-3'

CRT22 Forward Primer:
                                    (SEQ ID NO:3)
5'-HEX-TCGAGATGAAACCGAATGAAGAAA-3'

CRT22 Reverse Primer:
                                    (SEQ ID NO:4)
```

```
5'-GTTTCTTGGGACTGATATTGCCAAGTGGG-3'

ORS565 Forward Primer:
                                              (SEQ ID NO:5)
5'-TGGTCAACGGATTTAGAGTCAA-3'

ORS565 Reverse Primer:
                                              (SEQ ID NO:6)
5'-TCCAGTTTGGTCTTGATTTGG-3'

ORS732 Forward Primer:
                                              (SEQ ID NO:7)
5'-GCACGGAACTCCTCAAATGT-3'

ORS732 Reverse Primer:
                                              (SEQ ID NO:8)
5'-GCACGGGAAACAAAGAGTCA-3'
```

PCR Components:
4 ng gDNA
1×PCR buffer (Qiagen, Valencia, Calif.)
0.25 µM Forward primer
0.25 µM Reverse primer
1 mM MgCl$_2$
0.1 mM of each dNTP
0.4% PVP
0.04 Units HotStar Taq DNA polymerase (Qiagen, Valencia, Calif.)
Total Volume: 4.8 µl
Thermocycler Setup:
Step 1: 94° C. for 12 minutes
Step 2: 94° C. for 30 seconds
Step 3: 55° C. for 30 seconds
Step 4: 72° C. for 30 seconds
Step 5: repeat steps 2, 3 and 4 for 35 cycles
Step 6: 72° C. for 30 minutes SNP marker development: Eight pairs of primers were used to amplify eight genomic loci from both ONN687R and H757B/LS10760B-B-17-3-23-5 to develop SNP markers (Table 6). Three primer pairs (ZVG76snpF/R, ZVG77snpF/R, and ZVG78snpF/R) were designed based on sequences from restriction fragment length polymorphism (RFLP) probes ZVG76, ZVG77 and ZVG78 (Kolkman et al. 2007). Primer sequences for HT57F/R, HT64F/R, HT131F/R, HT134F/R, and HT210F/R were from Lai et al. (2005). SNPs were found in the amplicons from HT64F/R, HT210F/R, and ZVG78snpF/R. TaqMan MGB Allelic Discrimination assays were developed for one SNP locus in the HT64F/R amplicon and one SNP locus in the ZVG78snpF/R amplicon (See below), and the ONN687R×H757B/LS10760B-B-17-3-23-5 mapping population was genotyped with those two SNP markers using the developed TaqMan assays.

There were four SNP loci (marked in bold) in the HT64F/R amplicons from ONN687R and H757B/LS10760B-B-17-3-23-5. The TaqMan Assay was developed for the R-locus. The sequences for Forward Primer, Reverse Primer, Probe 1 and Probe 2 are 5'-CCGGCTGCTTCTAGACCTTATAAG-3' (SEQ ID NO:9), 5'-TCGTCGGTGGGACACACA-3' (SEQ ID NO: 10), 5'-6FAM-ACTGTTGGATCGGTTC-3'(SEQ ID NO: 11), and 5'-VIC-CACTGTTGGATCGATT-3'(SEQ ID NO: 12), respectively.

```
                                              (SEQ ID NO:13)
TTATTCTCGGCTTCCGGTGTGATTTTACTCTCATGGTTAAGTTTTCAAGA

GATTGTCGCY(T/C)GCTGAAAACTTTTTATATTGTTTCGGTATGATCTT

GGAGTTTATAGCCTTTGTAAGGTTAAGAATGAAACACCCGGCTGCTTCTA

GACCTTATAAGATACCCGTGGGCACTGTTGGATCGR(A/G)TTCTTCTGT

GTGTCCCACCGACGATTTTGATCTGTGTCGTGTTGGCTCTTTCTTCACTC

AAGGTCATGATCGTTAGY(T/C)GTY(C/T)ATTGCCATATTTTCGGGT

TCGCATTGCAACCGTTTTTAAAGTTTGCCGAGAAGAAAAGATGGCTTAAA

TTTTCAACTAAAGCCGATCTTCCCG
```

There were also four SNP loci (marked in bold) in the ZVG78snpF/R amplicons from ONN687R and H757B/LS10760B-B-17-3-23-5. The TaqMan Assay was developed for the R-locus at the 5' end. The sequences for Forward Primer, Reverse Primer, Probe 1 and Probe 2 are 5'-GTCCATCTTTCCTCAACGACTTG-3' (SEQ ID NO:14), 5'-CCTAAACGCCTCGAAAAAGCT-3'(SEQ ID NO: 15), 5'-6FAM-TTACCATGTCTATAATGC-3'(SEQ ID NO: 16), and 5'-VIC-ATTACCATGTCTGTAATGC-3'(SEQ ID NO: 17), respectively.

```
                                              (SEQ ID NO:18)
AACTGAGTTCTGTACGCCAGAGATTTGCCCGACCATGACCGCAGGTCCAA

AGTAAGTCTTGCTATTGCACATTTGCACGATTAACGGTTTCTTATATAGA

AGATACATGATTCTTGAATTTATGTAAATAAAACTTGACAGATATGAATA

CCGATGGGCTGATGGTGTGCAAATCAAGAAGCCTATTGAAGTTTCGGCTC

CAAAGTACGTAGAGTTCTTGATGGATTGGATTGAGTCACAATTGGATGAC

GAGTCCATCTTTCCTCAACGACTTGGTAATTAGTTAATTACCATGTCTR(

G/A)TAATGCATCATTTAATAAAGCTTTTTCGAGGCGTTTAGGAAACTGA

AATAGTAATTTTCGATTGY(T/C)CGTGCAGGAGCGCCATTTCCCGCCAA

TTTTAGGGACGTTGTGAAAACGATATTTAAACGCTTGTTTCGTGTATAY(

T/C)GCGCATATCTACCACACR(G/A)CATTTTCAGAAGATTGTGAGTCT

TAAAGAAGAAGCCCATCTAAACACTTGTTTCAAGCATTTCATATTGTTTA

CATGTGTAA
```

The following PCR setup was used for both SNP markers.
Real-Time PCR Components:
25 ng gDNA
1× Taqman Universal PCR Master Mix
22.5 µM Forward Primer
22.5 µM Reverse Primer
5 µM Probe 1
5 µM Probe 2
Total Volume: 25 µl
Bio-Rad iCycler Setup:
Step 1: 95° C. for 15 minutes
Step 2: 94° C. for 30 seconds
Step 3: 60° C. for 1 minute
Step 4: repeat steps 2 and 3 for 65 cycles
Step 5: 4° C. forever Indel marker development: Primers were designed to amplify and sequence 32 fatty acid related genes from the two parental lines ONN687R and H757B/LS10760B-B-17-3-23-5. Seven genes had polymorphisms, four genes had weak amplifications, and all others were monomorphic (Table 6). The mapping population ONN687R×H757B/LS10760B-B-17-3-23-5 was screened with all identified polymorphisms.

Mapping new markers and fine mapping low stearic acid QTL: JoinMap 3.0 (Van Ooij en, 2004a) was used to map all newly identified polymorphic markers. Marker CRT22 gave a significant segregation distortion and was not mapped. Six markers developed from the candidate gene approach mapped to chromosomes other than the target chromosome 17 (Table 6). Seven markers HA0442, ORS565, HT64, ZVG78, KASI-2, KASI-4, and ORS732 were mapped to chromosome 17. Fatty acid genes KASI-2 and KASI-4 were mapped to chromosome 17 but not close to the target low stearic acid QTL (FIG. 1). With the newly mapped markers, the low stearic QTL was fine mapped with MapQTL 5 ((Van Ooijen, 2004b) in the HA1875-ORS565 interval which spanned 27 cM in the upper telomeric region of LG 17. The fine mapped QTL had a significant LOD score of 23.2 and explained 50.8% of the variation in stearic acid content. The newly mapped markers can be used to facilitate the selection for low stearic acid in breeding program.

B) Developing and Mapping an Indel Marker for Palmitic Acid QTL

SNPs and indels were observed in the amplicon sequences of parental lines H280R[1]/687R-1-8-1 and OND163R with the primer pair for fatty acid gene KASII-2 (Table 6, FIG. 2). The mapping population H280R[1]/687R-1-8-1× OND163R was screened with this primer pair and amplicons were resolved on 3% Metaphor gels. Mapping program JoinMap 3.0 (Van Ooij en, 2004a) located this indel marker inside the low palmitic acid QTL on linkage group 5 (FIG. 3).

TABLE 5

List of markers investigated to saturate the low stearic acid QTL region.

| F Name | Sequence | R Name | Sequence | Note |
|---|---|---|---|---|
| 1) SSR | | | | |
| HA0953F-HEX | CAAACCAACAACCACCATCA (SEQ ID NO:34) | HA0953R | AAACGACACCGATGAGAACC (SEQ ID NO:35) | Monomorphic |
| HA1909F-FAM | CTGAGTTTCGTGTACCATTTCTATTG (SEQ ID NO:36) | HA1909R | ACACCAATCAGTGGGTTTCATC (SEQ ID NO:37) | Poor marker |
| HA0442F-HEX | TGGAACTGTAAATGGACCCAAG (SEQ ID NO:1) | HA0442 | GCACTGCACCATTTATGAGAAG (SEQ ID NO:2) | Polymorphic |
| CRT22F-HEX | TCGAGATGAAACCGAATGAAGAAA (SEQ ID NO:3) | CRT22R | GTTTCTTGGGACTGATATTGCCAAGTGGG (SEQ ID NO:4) | Polymorphic |
| ORS297F-FAM | TGCAAAGCTCACACTAACCTG | ORS297R | GTGTCTGCACGAACTGTGGT | Monomorphic |
| ZVG76ssrF-FAM | GCACCCTAGAGCTTCATTCG | ZVG76ssrR | AGCCCAAGGATGTTGTTTTG | Monomorphic |
| ORS565F | TGGTCAACGGATTTAGAGTCAA (SEQ ID NO:5) | ORS565R | TCCAGTTTGGTCTTGATTTGG (SEQ ID NO:6) | Polymorphic |
| ORS732F | GCACGGAACTCCTCAAATGT (SEQ ID NO:7) | ORS732R | GCACGGGAAACAAAGAGTCA (SEQ ID NO:8) | Polymorphic |
| 2) SNP | | | | |
| HT57F | GCGATTATTGTTATGGACGC (SEQ ID NO:19) | HT57R | AGCGGAAACTGTTCTTGTTG (SEQ ID NO:20) | Monomorphic |
| HT64F | TTATTCTCGGCTTCCGGT (SEQ ID NO:21) | HT64R | CGGGAAGATCGGCTTTAG (SEQ ID NO:22) | SNPs |
| HT131F | CGTAACATGCAAGTTGTGGA (SEQ ID NO:23) | HT131R | TGTACTCTAAACGGGCAACC (SEQ ID NO:24) | Monomorphic |
| HT134F | AGTCATGCTTGAAGGAGCTG (SEQ ID NO:25) | HT134R | CTCTGTCAGCTTGCAATGAA (SEQ ID NO:26) | Monomorphic |
| HT210F | CTAAAACTGTCGCAAGGGAA (SEQ ID NO:27) | HT210R | CCTCCATCAATGGTAAGCAC (SEQ ID NO:28) | SNPs |
| ZVG76snpF | TCCAACTCATGAACGGACTCT (SEQ ID NO:29) | ZVG76snpR | Same as ZVG76ssrR | Monomorphic |
| ZVG77snpF | TTGGTGACTCTTGCAGCATC (SEQ ID NO:30) | ZVG77snpR | AAGTTTAAAACCGCGTCGTG (SEQ ID NO:31) | Monomorphic |
| ZVG78snpF | TATGAGCCTCTTCGGTCTCG (SEQ ID NO:32) | ZVG78snpR | CACCTTATTCAGCCCCGATA (SEQ ID NO:33) | SNPS |

TABLE 6

Fatty acids genes investigated.

| Marker | Enzyme | Results on Stearic population | Map position |
|---|---|---|---|
| KASIII-1 | Ketoacyl-ACP Syntetase III | Co-dominant polymorphism | LG5 |
| KASIII-2 | Ketoacyl-ACP Syntetase III | Non-polymorphic | |
| KASIII-3 | Ketoacyl-ACP Syntetase III | Weak amplification | |
| KASI-1 | Ketoacyl-ACP Syntetase I | Non-polymorphic | |
| KASI-2 | Ketoacyl-ACP Syntetase I | Co-dominant polymorphism | LG17 |
| KASI-4 | Ketoacyl-ACP Syntetase I | Co-dominant polymorphism | LG17 |
| KASI-3 | Ketoacyl-ACP Syntetase I | Weak amplification | |
| KASII-1 | Ketoacyl-ACP Syntetase II | Non-polymorphic | |
| KASII-2 | Ketoacyl-ACP Syntetase II | Weak amplification | |
| KASII-3 | Ketoacyl-ACP Syntetase II | Co-dominant polymorphism | LG9 |
| KAR | Ketoacyl reductase | Non-polymorphic | |
| HAD | Hyroxyacyl-ACP dehydratase | Non-polymorphic | |
| Ear1 | Enoyl-ACP reductase | Non-polymorphic | |
| FATA-1 | FATA thioesterase | Non-polymorphic | |
| FATA-2 | FATA thioesterase | Non-polymorphic | |
| FATA-3 | FATA thioesterase | Dominant polymosphism | LG7 |
| FATB-1 | FATB thioesterase | Weak amplification | |
| FATB-2 | FATB thioesterase | Non-polymorphic | |
| CT-alpha1 | ACC->carboxyltransferase-alpha (accA) | Dominant polymorphism | LG10 |
| BCCP | ACC->biotin carboxyl carrier protein (aacB) | Non-polymorphic | |
| KCS1 | Ketoacyl-CoA synthase-I | Non-polymorphic | |
| KCS2 | Ketoacyl-CoA synthase-II | Non-polymorphic | |
| KCS3 | Ketoacyl-CoA synthase-III | Non-polymorphic | |
| SAD 17 | Stearoyl-ACP desaturase | Co-dominant polymorphism | LG1 |
| erLPAT | Lysophosphatidic acid acyl transferase | Non-polymorphic | |
| erPAP | Phophatidic acid acyl transferase | Non-polymorphic | |
| PDPS | Phosphatidylglycerophosphatase synthase | Non-polymorphic | |
| erLDS | ER linoleate desaturase | Non-polymorphic | |
| FAD6-1 | Plastid oleate desaturase | Non-polymorphic | |
| FAD6-2 | Plastid oleate desaturase | Non-polymorphic | |
| FAD2-1F5-R2 | Oleate desaturase | Non-polymorphic | |
| FAD2-1F5-R3 | Oleate desaturase | Non-polymorphic | |

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An oil extracted from seeds of one or more individuals of a sunflower cultivar that has been stabilized for seed oil fatty acid profile, wherein the seed oil comprises:
   a fatty acid profile comprising 10% or less total combined palmitic acid and stearic acid content and 15% or more linoleic acid content; and wherein the genome of the sunflower cultivar and the seed oil extracted therefrom comprises the polynucleotide of SEQ ID NO:13, wherein the nucleotide at position 60 of the polynucleotide of SEQ ID NO:13 is a cytosine (C), the nucleotide at position 181 of the polynucleotide of SEQ ID NO:13 is a guanine (G), the nucleotide at position 258 of the polynucleotide of SEQ ID NO:13 is a cytosine (C), and the nucleotide at position 261 of the polynucleotide of SEQ ID NO:13 is a thymine (T), and the polynucleotide of SEQ ID NO:18, wherein the nucleotide at position 299 of the polynucleotide of SEQ ID NO:18 is an adenine (A), the nucleotide at position 364 of the polynucleotide of SEQ ID NO:18 is a cytosine (C), the nucleotide at position 439 of the polynucleotide of SEQ ID NO:18 is a cytosine (C), and the nucleotide at position 457 of the polynucleotide of SEQ ID NO:18 is an adenine (A).

* * * * *